(12) United States Patent
Nabutovsky et al.

(10) Patent No.: US 8,065,001 B1
(45) Date of Patent: Nov. 22, 2011

(54) USE OF IMPLANTABLE BODY POSITION AND BODY MOVEMENT SENSORS

(75) Inventors: Yelena Nabutovsky, Mountain View, CA (US); Eric Falkenberg, Simi Valley, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 565 days.

(21) Appl. No.: 11/681,047

(22) Filed: Mar. 1, 2007

(51) Int. Cl.
*A61N 1/08* (2006.01)

(52) U.S. Cl. .......................................... 607/17

(58) Field of Classification Search .................... 600/17; 607/19
See application file for complete search history.

(56) References Cited

U.S. PATENT DOCUMENTS

| | | | | |
|---|---|---|---|---|
| 4,846,195 A | * | 7/1989 | Alt ................. | 600/595 |
| 5,014,704 A | * | 5/1991 | Alt ................. | 607/19 |
| 5,342,404 A | * | 8/1994 | Alt et al. ............ | 607/6 |
| 5,387,229 A | * | 2/1995 | Poore ............... | 607/18 |
| 5,413,592 A | | 5/1995 | Schroeppel | |
| 5,549,650 A | | 8/1996 | Bornzin et al. | |
| 5,562,711 A | * | 10/1996 | Yerich et al. ........ | 607/17 |
| 6,122,536 A | * | 9/2000 | Sun et al. .......... | 600/341 |
| 6,188,927 B1 | | 2/2001 | Lu et al. | |
| 6,295,471 B1 | | 9/2001 | Bornzin et al. | |
| 6,466,821 B1 | | 10/2002 | Pianca et al. | |
| 6,625,490 B1 | | 9/2003 | McClure et al. | |
| 6,625,493 B2 | | 9/2003 | Kroll et al. | |
| 6,937,900 B1 | | 8/2005 | Pianca et al. | |
| 2003/0055461 A1 | * | 3/2003 | Girouard et al. ...... | 607/17 |
| 2004/0039295 A1 | * | 2/2004 | Olbrich et al. ........ | 600/538 |
| 2006/0030892 A1 | * | 2/2006 | Kadhiresan et al. ..... | 607/19 |
| 2006/0253042 A1 | * | 11/2006 | Stahmann et al. ...... | 600/508 |

OTHER PUBLICATIONS

Non-Final Office Action mailed May 26, 2009: Related U.S. Appl. No. 11/681,033.

* cited by examiner

*Primary Examiner* — Niketa Patel
*Assistant Examiner* — Hiba El-Kaissi
(74) *Attorney, Agent, or Firm* — Theresa Takeuchi; Steven M. Mitchell

(57) ABSTRACT

Implantable systems, and methods for use therewith, are provided for using an implantable sensor for detecting body position and/or body movement, and using what is learned therefrom to improve accuracy of an implantable sensor that is sensitive to at least one of body position and/or body movement. Also provided are implantable systems, and methods for use therewith, that detect body position and/or body movement in order to monitor a condition and/or detect specific episodes. Other embodiments are also provided.

21 Claims, 10 Drawing Sheets

USE OF IMPLANTABLE BODY POSITION AND BODY MOVEMENT SENSORS

RELATED APPLICATION

This application relates to commonly invented and commonly assigned U.S. patent application Ser. No. 11/881,033, entitled USE OF IMPLANTABLE SENSORS FOR PROPRIOCEPTION AND ACCURATE SENSOR DETECTION, now U.S. Pat. No. 7,848,810, filed the same day as the present application.

FIELD OF THE INVENTION

Embodiments of the present invention relate to implantable sensors that are sensitive to body position and/or other body movement, and implantable sensors that are designed to detect body position and/or body movement.

BACKGROUND

More and more implantable sensors are being used, developed, or proposed. Such implantable sensors can be used to detect physiologic, cardiac and other related parameters of a patient for the purpose of monitoring such parameters and/or using such parameters as feedback for adjusting other parameters of implantable devices, such as for adjusting pacing parameters of pacemakers. However, many such implantable sensors are sensitive to a patient's body position and/or body movement. Examples of such implantable sensors include photoplethysmography (PPG) sensors, left atrial pressure (LAP) sensors, impedance sensors and cardio-mechanical sensors (CMES), but are not limited thereto.

Data collected by an implantable sensor that is sensitive to body position and/or body movement may provide inaccurate readings, which can adversely affect its monitoring and/or feedback capabilities. For example, determinations of patient condition status and alarms that are based on such sensor readings can become inaccurate, resulting in incorrect adjustments to sensor-based therapy and/or false positives and false negatives.

Therefore, there is a need to prevent the above mentioned potential problems associated with implantable sensors that are sensitive to a patient's body position and/or body movement.

Sensors, such as accelerometers and position sensors are available for detecting body movement and/or body position. Typically, accelerometers provide feedback regarding a patient's activity level, so that pacing rates can be adjusted to meet the metabolic demands of the body. Since these sensors are already incorporated into many implantable devices, it would be beneficial and relatively simple to use them for additional purposes.

SUMMARY OF THE INVENTION

Specific embodiments of the present invention are directed to implantable systems, and methods for use therewith, for improving the accuracy of an implantable sensor that is sensitive to at least one of body position and body movement. In accordance with an embodiment, a first implantable sensor is used to obtain a sensor signal indicative of a parameter of interest that is used, e.g., for at least one of monitoring and feedback, where the first implantable sensor is sensitive to at least one of body position and body movement. At least one further implantable sensor is used to detect at least one of body position and body movement. Based on the at least one of body position and body movement detected by the at least one further implantable sensor, there is a determination as to an extent to which to filter or otherwise process the sensor signal obtained using the first implantable sensor. The sensor signal can then be filtered or otherwise processed to the determined extent, prior to using the sensor signal (e.g., for the at least one of monitoring and feedback).

In a specific embodiment, the at least one further implantable sensor is used to detect the body position of the patient. A first level of filtering and/or other signal processing is used if it is determined that the patient is supine, and second level of filtering and/or other signal processing is used if it is determined that the patient is not supine, where the second level is greater than the first level.

In another embodiment, the at least one further implantable sensor is used to detect the activity level of the patient. A first level of filtering and/or other signal processing is used if it is determined that the activity level of the patient does not exceed a threshold, and a second level of filtering and/or other signal processing is used if it is determined that the activity level of the patient exceeds the threshold, where the second level is greater than the first level.

In accordance with specific embodiments, the patient's heart rate is also monitored. In such embodiments, an extent to which to filter or otherwise process the sensor signal obtained using the first implantable sensor can be determined based on the at least one of body position and body movement detected by the at least one further implantable sensor and the patient's heart rate.

In accordance with further embodiments of the present invention, there is a determination of at least one of how to interpret and how to use the sensor signal obtained using the first implantable sensor, based on the at least one of body position and body movement detected by the at least one further implantable sensor.

In specific embodiments, data indicative of the parameter of interest is stored along with data indicative of at least one of body position and body movement of the patient, so that when the data indicative of the parameter of interest is analyzed the corresponding at least one of body position and body movement of the patient can be identified.

In accordance with other embodiments of the present invention, a first implantable sensor is used to obtain a sensor signal indicative of a parameter of interest, e.g., that is used for at least one of monitoring and feedback, where the first implantable sensor is sensitive to body position. At least one further implantable sensor is used to detect body position. A determination of whether to utilize the sensor signal obtained using the first implantable sensor is made based on the body position detected by the at least one further implantable sensor. This can include putting the first implantable sensor in standby mode when the body position, as detected using the at least one further implantable sensor, is not a desired body position.

In accordance with still other embodiments of the present invention, data is stored that is indicative of at least one of body position and body movement detected over an extended period of time, and a determination of a condition (e.g., cardiac disease status) of a patient is based on the stored data. This can include determining whether a condition has improved, worsened or generally stayed the same. In specific embodiments, a histogram is produced that is indicative of at least one of body position and body movement over an extended period of time, and the condition of the patient is determined based on the histogram.

Specific embodiments of the present invention can be used to detect periods of orthostatic hypotension. At least one implantable sensor is used to monitor a patient's body position, and at least one further implantable sensor is used to monitor the patient's blood pressure. Periods of orthostatic hypotension are detected based on the monitored body position and blood pressure. A treatment can be triggered in response to detecting a period of orthostatic hypotension. Also, data indicative of detected periods of orthostatic hypotension can be stored for later analysis.

This description is not intended to be a complete description of, or limit the scope of, the invention. Other features, aspects, and objects of the invention can be obtained from a review of the specification, the figures, and the claims.

DETAILED DESCRIPTION

The following detailed description of the embodiments of present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims.

It would be apparent to one of skill in the art that the embodiments of the present invention, as described below, may be implemented in many different embodiments of hardware, software, firmware, and/or the entities illustrated in the figures. Any actual software and/or hardware described herein is not limiting of the present invention. Thus, the operation and behavior of the present invention will be described with the understanding that modifications and variations of the embodiments are possible, given the level of detail presented herein.

Various implantable sensors for detecting body position (also known as proprioception) and/or body movement (e.g., activity or motion) are available, are being developed and/or have been proposed. Examples of such sensors are disclosed in the following patents, each of which are incorporated herein by reference: U.S. Pat. No. 6,658,292 (Kroll et al.), entitled "Detection of Patient's Position and Activity Status using 3D Accelerometer-Based Position Sensor"; U.S. Pat. No. 6,625,493 (Kroll et al.), entitled "Orientation of Patient's Position Sensor using External Field"; and U.S. Pat. No. 6,466,821 (Pianca et al.), entitled "AC/DC Multi-Axis Accelerometer for Determining Patient Activity and Body Position." As described in these patents, the outputs of such sensors are generally being used, or have been proposed to be used, for selecting cardiac pacing rates, cardiac pacing stimulation levels, and types of cardiac pacing. Accordingly, more and more implantable cardiac devices are likely to include such sensors. Less sophisticated body movement (e.g., activity or motion) sensors have also been used and/or proposed. Embodiments of the present invention, as will be described below, take further advantage of the presence of such body position and/or body movement sensors.

Exemplary Implantable Cardiac Device

Figure 1:
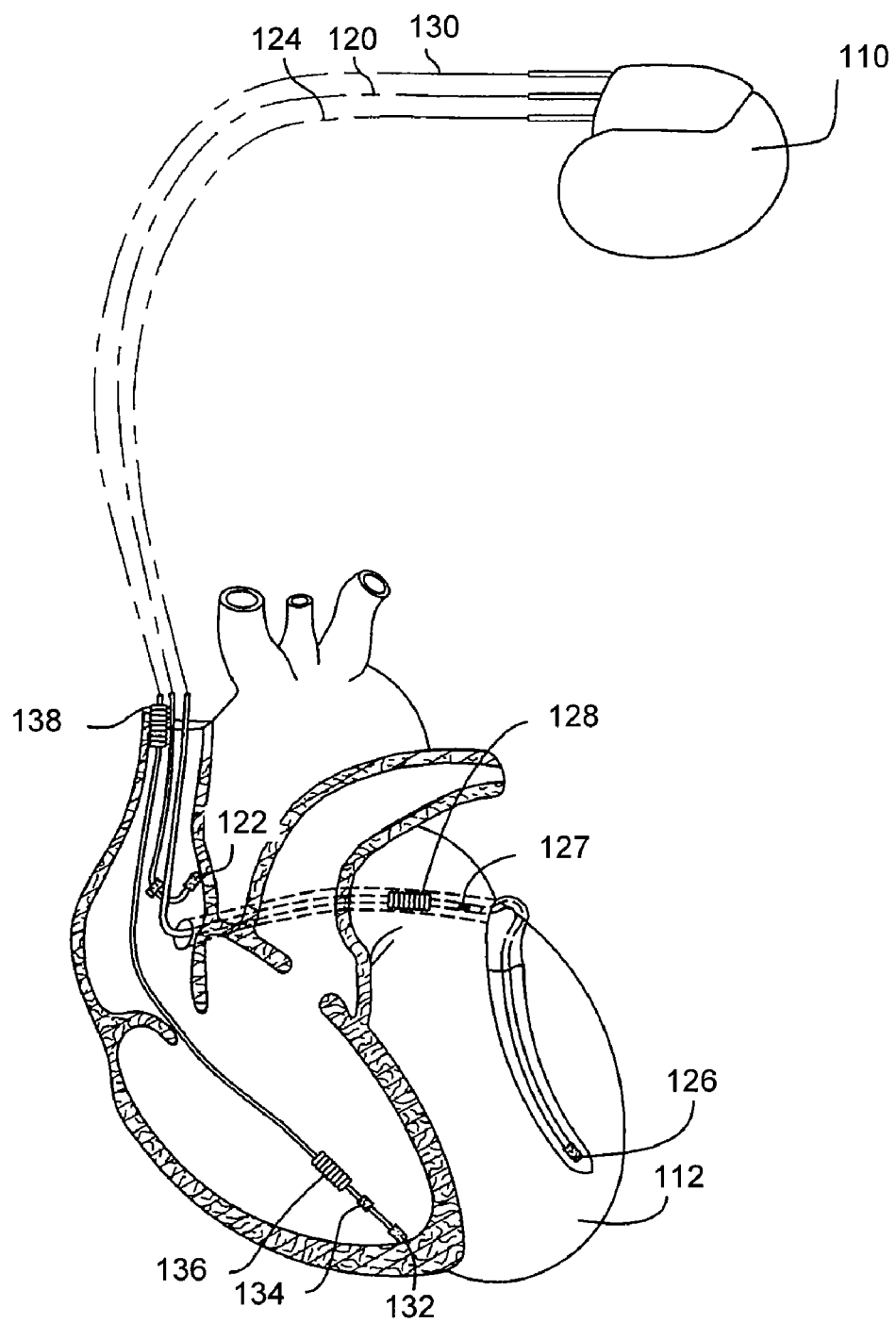
FIG. 1 is a simplified diagram illustrating an exemplary ICD in electrical communication with a patient's heart.

Before describing specific embodiments of the present invention in further detail, it is useful to first describe an exemplary environment in which the invention may be implemented. Referring to FIG. 1, an exemplary implantable cardiac device 110 (also referred to as a pacing device, a pacing apparatus, a stimulation device, or simply a device) is in electrical communication with a patient's heart 112 by way of three leads, 120, 124 and 130, suitable for delivering multi-chamber stimulation. While not necessary to perform embodiments of the present invention, the exemplary device 110 is also capable of delivering shock therapy.

To sense atrial cardiac signals and to provide right atrial chamber stimulation therapy, the stimulation device 110 is coupled to an implantable right atrial lead 120 having at least an atrial tip electrode 122, which typically is implanted in the patient's right atrial appendage. To sense left atrial and ventricular cardiac signals and to provide left-chamber pacing therapy, the stimulation device 110 is coupled to a "coronary sinus" lead 124 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 124 is designed to receive left atrial and ventricular cardiac signals and to deliver left atrial and ventricular pacing therapy using at least a left ventricular tip electrode 126, left atrial pacing therapy using at least a left atrial ring electrode 127, and shocking therapy using at least a left atrial coil electrode 128. Embodiments of the present invention may of course be practiced with a coronary sinus lead that does not include left atrial sensing, pacing or shocking electrodes.

The stimulation device 110 is also shown in electrical communication with the patient's heart 112 by way of an implantable right ventricular lead 130 having, in this embodiment, a right ventricular tip electrode 132, a right ventricular ring electrode 134, a right ventricular (RV) coil electrode 136, and an SVC coil electrode 138. Typically, the right ventricular lead 130 is transvenously inserted into the heart 112 so as to place the right ventricular tip electrode 132 in the right ventricular apex so that the RV coil electrode 136 will be positioned in the right ventricle and the SVC coil electrode 138 will be positioned in the superior vena cava. Accordingly, the right ventricular lead 130 is capable of receiving cardiac signals and delivering stimulation in the form of pacing and shock therapy to the right ventricle. It will be understood by those skilled in the art that other lead and electrode configurations such as epicardial leads and electrodes may be used.

Figure 2:
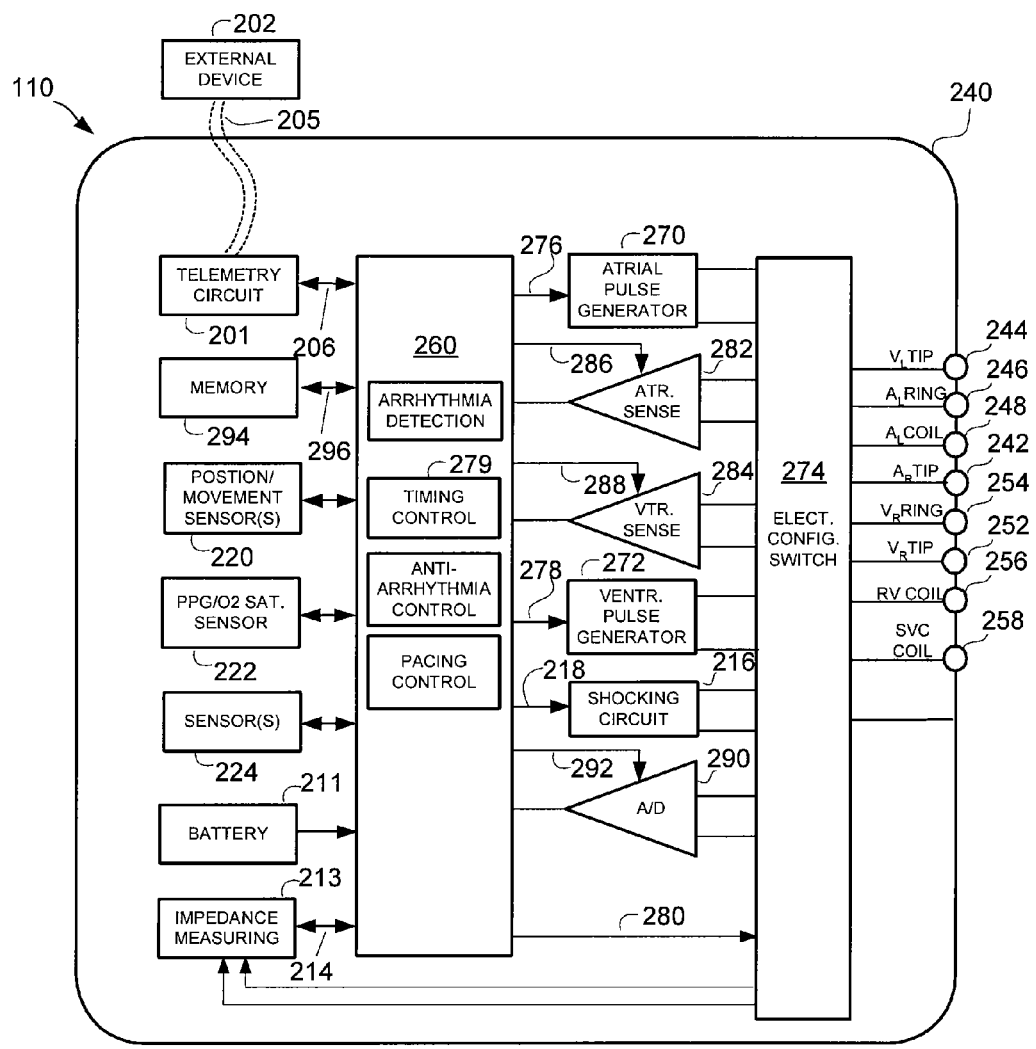
FIG. 2 is a functional block diagram of an exemplary ICD that can provide cardioversion, defibrillation, and pacing stimulation in four chambers of a heart.

As illustrated in FIG. 2, a simplified block diagram is shown of the multi-chamber implantable pacing device 110, which is capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation.

The housing 240 for the pacing device 110, shown schematically in FIG. 2, is often referred to as the "can", "case" or "case electrode" and may be programmably selected to act as the return electrode for all "unipolar" modes. The housing 240 may further be used as a return electrode alone or in combination with one or more of the coil electrodes, 128, 136 and 138, for shocking purposes. The housing 240 further includes a connector (not shown) having a plurality of terminals, 242, 244, 246, 248, 252, 254, 256, and 258 (shown schematically and, for convenience, the names of the electrodes to which they are connected are shown next to the terminals). As such, to achieve right atrial sensing and pacing, the connector includes at least a right atrial tip terminal (AR TIP) 242 adapted for connection to the atrial tip electrode 122.

To achieve left atrial and ventricle sensing, pacing and shocking, the connector includes at least a left ventricular tip terminal (VL TIP) 244, a left atrial ring terminal (AL RING) 246, and a left atrial shocking terminal (AL COIL) 148, which are adapted for connection to the left ventricular ring electrode 126, the left atrial tip electrode 127, and the left atrial coil electrode 128, respectively.

To support right ventricle sensing, pacing and shocking, the connector further includes a right ventricular tip terminal (VR TIP) 252, a right ventricular ring terminal (VR RING) 254, a right ventricular shocking terminal (RV COIL) 256, and an SVC shocking terminal (SVC COIL) 258, which are adapted for connection to the right ventricular tip electrode 132, right ventricular ring electrode 134, the RV coil electrode 136, and the SVC coil electrode 138, respectively.

At the core of the pacing device 110 is a programmable microcontroller 260 which controls the various types and modes of stimulation therapy. As is well known in the art, the microcontroller 260 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 260 includes the ability to process or monitor input signals (data) as controlled by a program code stored in a designated block of memory. The details of the design of the microcontroller 260 are not critical to the present invention. Rather, any suitable microcontroller 260 can be used to carry out the functions described herein. The use of microprocessor-based control circuits for performing timing and data analysis functions are well known in the art. In specific embodiments of the present invention, the microcontroller 260 performs some or all of the steps associated with arrhythmia detection, selecting an appropriate anti-arrhythmia therapy, performing a mode switch from an atrial tracking ventricular pacing mode to a non-atrial tracking ventricular pacing mode, as well as maintaining a high percentage of pacing during mode switch.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the pacing device and their inter-relationship, see U.S. Pat. No. 4,788,980 (Mann et. al.). The '052, '555, '298 and '980 patents are incorporated herein by reference.

An atrial pulse generator 270 and a ventricular pulse generator 272 generate pacing stimulation pulses for delivery by the right atrial lead 120, the right ventricular lead 130, and/or the coronary sinus lead 124 via an electrode configuration switch 274. It is understood that in order to provide stimulation therapy in each of the four chambers of the heart, the atrial and ventricular pulse generators, 270 and 272, may include dedicated, independent pulse generators, multiplexed pulse generators, or shared pulse generators. The pulse generators, 270 and 272, are controlled by the microcontroller 260 via appropriate control signals, 276 and 278, respectively, to trigger or inhibit the stimulation pulses.

The microcontroller 260 further includes timing control circuitry 279 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The implantable device 110 is also shown as including one or more sensor 220 that is used to detect a patient body position and/or body movement (e.g., activity or motion). Examples of such sensors that are capable of detecting both patient body position and body movement are disclosed in the following patents: U.S. Pat. No. 6,658,292 (Kroll et al.), entitled "Detection of Patient's Position and Activity Status using 3D Accelerometer-Based Position Sensor"; U.S. Pat. No. 6,625,493 (Kroll et al.), entitled "Orientation of Patient's Position Sensor using External Field"; and U.S. Pat. No. 6,466,821 (Pianca et al.), entitled "AC/DC Multi-Axis Accelerometer for Determining Patient Activity and Body Position," each of which were incorporated herein by reference above. Use of other sensor capable of detecting patient position and/or patient movement are also within the scope of the present invention.

Where there is only a need to detect body movement (e.g., activity or motion), but not necessarily body position, a simpler lower power activity sensor, such as a passive activity sensor may be used to obtain information relating to the physical activity of the patient. A passive activity sensor can convert mechanical motion into a detectable electrical signal (e.g., a BEMF signal) without requiring an external excitation current or voltage. However, some parasitic current will still be necessary to measure the electrical signal produced by such a passive activity sensor. Such parasitic current is typically very low, e.g., on the order of 5 to 15 μA. A widely used passive activity sensor incorporates a piezoelectric crystal which generates a measurable electrical potential when a mechanical stress resulting from physical activity is applied to the sensor. Examples of these are described in U.S. Pat. No. 4,140,132 (Dahl), entitled "Variable Rate Timer for a Cardiac Pacemaker" and U.S. Pat. No. 4,428,378 (Anderson et al.), entitled "Rate Adaptive Pacer," which are incorporated herein by reference. Another type of passive activity sensor includes use a cantilever beam having a film of a piezoelectric polymer adhered to a surface of the beam, rather than a piezoelectric crystal. Examples of this are described in U.S. Pat. No. 5,833,713 (Moberg), entitled "Rate-Responsive Implantable Stimulation Device having a Miniature Hybrid-Mountable Accelerometer-Based Sensor and Method of Fabrication" and U.S. Pat. No. 5,383,473 (Moberg), entitled "Rate Responsive Pacemaker having an Accelerometer-based Physical Activity Sensor," which are incorporated herein by reference. A further type of a passive activity sensor includes a magnet assembly and a conductive coil that moves relative to the magnet assembly in response to motion. An example of this is described in U.S. Pat. No. 5,792,199 (Fayram et al.), entitled "Pacemaker having Rate Responsive Transducer and Method for Operating Same," which is incorporated herein by reference. These are just a few examples of the types of passive activity sensor that could be included within the device 110. Using one dimensional activity information (i.e., acceleration) obtained by the passive activity sensor, the microcontroller 260 can detect body movement, but not body position. Use of other sensors capable of detecting patient movement are also within the scope of the present invention.

The device 110 is also shown as including a photoplethysmography (PPG) and/or oxygen saturation sensor 222. Such a sensor 222 generally includes a light source that generates light of one or more wavelengths (e.g., 660 nm and 940 nm) and a light detector. Exemplary implantable PPG sensors capable of being used to measure oxygen saturation levels are disclosed in following patents, both of which are incorporated herein by reference: U.S. Pat. No. 6,491,639 entitled "Extravascular Hemodynamic Sensor" (Turcott) and U.S. Pat. No. 6,480,733 entitled "Method for Monitoring Heart Failure" (Turcott). PPG/oxygen saturation sensors can be incorporated into a device housing (e.g., 240) or incorporated into a separated housing that is attached to a device housing. PPG/oxygen saturation sensors can also be located on a lead or catheter, thereby enabling the sensor 222 to be located within the heart, within an artery or within a vein. Examples of such sensors are disclosed in U.S. patent application Ser. No. 11/231,555 (Poore), entitled "Implantable Multi-Wavelength Oximeter Sensor", filed Sep. 20, 2005, which is incorporated herein by reference. Depending upon where the sensor is located, it can be used to detect venous or arterial oxygen saturation. A PPG sensor can also be used, depending upon where it is located, to detect respiration, episodes of apnea, heart failure status, etc. Such sensors are typically sensitive to patient position and patient movement.

The device 110 can also include further sensors 224, such as but not limited to, sensors capable of measuring left atrial pressure (LAP), other pressure sensors, an impedance sensor, a CMES sensor, a glucose sensor, etc. Such sensors 224, or portions thereof, can be located within the housing 240, while other such sensors, or portion thereof, can be located on a lead or within another housing attached to the housing 240. It is also possible that an entire sensor 224 be located on a lead or within a separate housing. Many of these sensors may be sensitive to a patient's body position and/or body movement.

The device 110 is also shown as having an impedance measuring circuit 213 which is enabled by the microcontroller 260 via a control signal 214. The known uses for an impedance measuring circuit/sensor 213 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; measuring thoracic impedance for detecting and assessing the severity of pulmonary edema; detecting when the device has been implanted; measuring stroke volume; and detecting the opening of heart valves, etc. The impedance measuring circuit/sensor 213 is advantageously coupled to the switch 274 so that any desired electrode may be used. In addition, to facilitate the measurement of peripheral tissue edema, extra electrodes can be added to the device housing, thereby limiting the test electric field to the peripheral tissue.

The switch bank 274 includes a plurality of switches for connecting the desired electrodes to the appropriate I/O circuits, thereby providing complete electrode programmability. Accordingly, the switch 274, in response to a control signal 280 from the microcontroller 260, determines the polarity of the stimulation pulses (e.g., unipolar, bipolar, etc.) by selectively closing the appropriate combination of switches (not shown) as is known in the art.

Atrial sensing circuits 282 and ventricular sensing circuits 284 may also be selectively coupled to the right atrial lead 120, coronary sinus lead 124, and the right ventricular lead 130, through the switch 274 for detecting the presence of cardiac activity in each of the four chambers of the heart. Accordingly, the atrial (ATR. SENSE) and ventricular (VTR. SENSE) sensing circuits, 282 and 284, may include dedicated sense amplifiers, multiplexed amplifiers, or shared amplifiers. The switch 274 determines the "sensing polarity" of the cardiac signal by selectively closing the appropriate switches, as is also known in the art. In this way, the clinician may program the sensing polarity independent of the stimulation polarity.

Each sensing circuit, 282 and 284, preferably employs one or more low power, precision amplifiers with programmable gain and/or automatic gain control, bandpass filtering, and a threshold detection circuit, as known in the art, to selectively sense the cardiac signal of interest. The automatic gain control enables the device 110 to deal effectively with the difficult problem of sensing the low amplitude signal characteristics of atrial or ventricular fibrillation. Such sensing circuits, 282 and 284, can be used to determine cardiac performance values used in the present invention. Alternatively, an automatic sensitivity control circuit may be used to effectively deal with signals of varying amplitude.

The outputs of the atrial and ventricular sensing circuits, 282 and 284, are connected to the microcontroller 260 which, in turn, are able to trigger or inhibit the atrial and ventricular pulse generators, 270 and 272, respectively, in a demand fashion in response to the absence or presence of cardiac activity, in the appropriate chambers of the heart. The sensing circuits, 282 and 284, in turn, receive control signals over signal lines, 286 and 288, from the microcontroller 260 for purposes of measuring cardiac performance at appropriate times, and for controlling the gain, threshold, polarization charge removal circuitry (not shown), and timing of any blocking circuitry (not shown) coupled to the inputs of the sensing circuits, 282 and 286.

For arrhythmia detection, the device 110 utilizes the atrial and ventricular sensing circuits, 282 and 284, to sense cardiac signals to determine whether a rhythm is physiologic or pathologic. The timing intervals between sensed events (e.g., P-waves, R-waves, and depolarization signals associated with fibrillation) are then classified by the microcontroller 260 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 290. The data acquisition system 290 is configured to acquire intracardiac electrogram signals, convert the raw analog data into a digital signal, and store the digital signals for later processing and/or telemetric transmission to an external device 202. The data acquisition system 290 is coupled to the right atrial lead 120, the coronary sinus lead 124, and the right ventricular lead 130 through the switch 274 to sample cardiac signals across any pair of desired electrodes.

Advantageously, the data acquisition system 290 can be coupled to the microcontroller 260, or other detection circuitry, for detecting an evoked response from the heart 212 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 260 detects a depolarization signal during a window following a stimulation pulse, the presence of which indicates that capture has occurred. The microcontroller 260 enables capture detection by triggering the ventricular pulse generator 272 to generate a stimulation pulse, starting a capture detection window using the timing control circuitry 279 within the microcontroller 260, and enabling the data acquisition system 290 via control signal 292 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 260 is further coupled to a memory 294 by a suitable data/address bus 296, wherein the programmable operating parameters used by the microcontroller 260 are stored and modified, as required, in order to customize the operation of the pacing device 110 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 212 within each respective tier of therapy Advantageously, the operating parameters of the implantable device 110 may be non-invasively programmed into the memory 294 through a telemetry circuit 201 in telemetric communication with the external device 202, such as a programmer, transtelephonic transceiver, or a diagnostic system analyzer. The telemetry circuit 201 can be activated by the microcontroller 260 by a control signal 206. The telemetry circuit 201 advantageously allows intracardiac electrograms and status information relating to the operation of the device 110 (as contained in the microcontroller 260 or memory 294) to be sent to an external device 202 through an established communication link 204.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

In the case where the pacing device 110 is also intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 260 further controls a shocking circuit 216 by way of a control signal 218. The shocking circuit 216 generates shocking pulses of low (up to 0.5 Joules), moderate (0.5-10 Joules), or high energy (11 to 40 Joules), as controlled by the microcontroller 260. Such shocking pulses are applied to the patient's heart 212 through at least two shocking electrodes, and as shown in this embodiment, selected from the left atrial coil electrode 228, the RV coil electrode 236, and/or the SVC coil electrode 238. As noted above, the housing 240 may act as an active electrode in combination with the RV electrode 236, or as part of a split electrical vector using the SVC coil electrode 238 or the left atrial coil electrode 228 (i.e., using the RV electrode as a common electrode).

The pacing device 110 additionally includes a battery 211 which provides operating power to all of the circuits shown in FIG. 2. If the pacing device 110 also employs shocking therapy, the battery 211 should be capable of operating at low current drains for long periods of time, and then be capable of providing high-current pulses (for capacitor charging) when the patient requires a shock pulse. The battery 211 should also have a predictable discharge characteristic so that elective replacement time can be detected.

The above described implantable stimulation device 110 was described as an exemplary pacing device. One or ordinary skill in the art would understand that embodiments of the present invention can be used with alternative types of implantable devices. Accordingly, embodiments of the present invention should not be limited to use only with the above described device.

Typically, the greater the amount of filtering and/or other signal processing, the greater the amount of power consumption. Additionally, excess filtering and/or other signal processing may end up masking or averaging out important information in a signal. Accordingly, where possible, it is preferred that more filtering and/or other signal processing than necessary not occur. Nevertheless, where a signal is highly sensitive to body position and/or body motion, it may be better to increase the filtering and/or other processing of the signal than to either use it as-is or not use it at all.

FIG. 3

Specific embodiments of the present invention relate to using a body position and/or body movement (e.g., activity or motion) sensor to determine to what extent to filter or otherwise process a signal obtained using another implantable sensor that is sensitive to body position and/or activity. Such embodiments will now be explained with reference to the high level flow diagram of FIG. 3.

Figure 3:
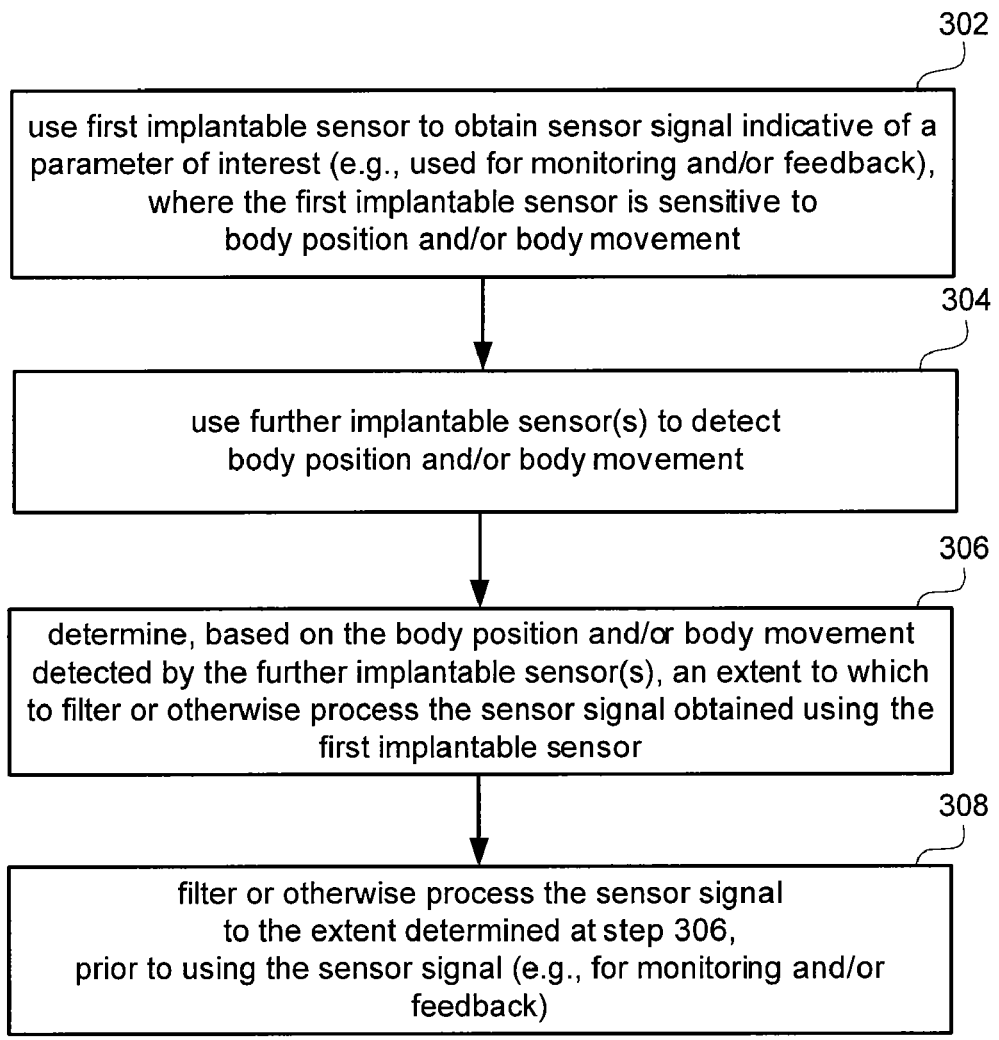
FIG. 3 is a high level flow diagram useful for describing embodiments of the present invention where one or more implantable body position and/or body movement sensor is used to determine an extent to which to filter or otherwise process a sensor signal of interest obtained using an implantable sensor that is sensitive to body position and/or body movement.

Referring to FIG. 3, at a step 302, a first implantable sensor is used to obtain a sensor signal indicative of a parameter of interest (e.g., that may be used for monitoring and/or feedback), where the first implantable sensor is sensitive to body position and/or body movement. Examples of such a first implantable sensor include, but are not limited to, a PPG sensor, a pulse oximetry sensor, a pressure sensor (e.g., for measuring left atrial pressure), a venous O2 saturation sensor, an arterial O2 saturation sensor, and a glucose sensor. The sensor signal generated by the first implantable sensor can be an analog signal, a digital representation of an analog signal generated by the first implantable sensor, or a digital signal generated by the first implantable sensor (where the output of the first implantable sensor is digital). The sensor signal can be indicative of, e.g., a hemodynamic, physiologic, respiratory or rhythmic cardiac function, such as, but not limited to respiration, left atrial pressure, right atrial pressure, thoracic impedance, arterial O2 saturation, ventricular O2 saturation, photoplethysmography, mechanical contractility, heart sounds, blood glucose concentration, mechanical synchrony, cardiogenic impedance. The sensor signal can alternatively be indicative of other parameters, while still being within the scope of the present invention.

Still referring to FIG. 3, at a step 304 at least one further implantable sensor is used to detect body position and/or body movement (e.g., activity or motion). As mentioned above, in the discussion of FIG. 2, such sensor(s) can be, but are not limited to, those described in: U.S. Pat. No. 6,658,292 (Kroll et al.), entitled "Detection of Patient's Position and Activity Status using 3D Accelerometer-Based Position Sensor"; U.S. Pat. No. 6,466,821 (Kroll et al.), entitled "Orientation of Patient's Position Sensor using External Field"; and U.S. Pat. No. 6,625,493 (Pianca et al.), entitled "AC/DC Multi-Axis Accelerometer for Determining Patient Activity and Body Position", each of which was incorporated herein by reference above. If the desire is to only detect patient activity, then simpler activity sensors, many of which were discussed above, can be used.

At a step 306, an extent to which to filter or otherwise process the sensor signal obtained using the first implantable sensor is determined, based on the body position and/or body movement detected by the further implantable sensor(s). Referring to FIG. 2, the determination at step 306 can be performed, e.g., by the microcontroller 260, or by some other hardware, or by software, firmware, or combinations thereof.

At a step 308, the sensor signal obtained at step 304 is filtered or otherwise processed to the extent determined at step 306, prior to using the sensor signal (e.g., for monitoring and/or feedback). The filtering and/or other signal processing can be performed by the microcontroller 260, or by a dedicated filter, a digital signal processor (DSP), some other hardware, software, firmware, or combinations thereof. The filtering or other processing of a sensor signal can involve filtering an analog sensor signal, filtering a digital representation of an analog sensor signal, or filtering of a digital sensor signal.

In a specific embodiment useful where the first implantable sensor is primarily sensitive to body movement, step 304 involves using the further implantable sensor(s) to detect body movement, and step 306 involves determining, based on the body movement detected by the further implantable sensor(s), an extent to which to filter or otherwise process the sensor signal obtained using the first implantable sensor. The further implantable sensor(s) that detects body movement can determine whether the patient is active, or not active. However, it is also within the scope of the present invention that multiple levels of activity can be detected. Where there is a determination at step 304 of the activity level of the patient, step 306 can include using a first level of filtering and/or other signal processing if it is determined that the activity level of the patient does not exceed a threshold, and using a second level of filtering and/or other signal processing if it is determined at step 306 that the activity level of the patient exceeds the threshold, where the second level of filtering and/or other signal processing is greater than the first level of filtering and/or other signal processing. It is also within the scope of the present invention that one level of filtering be no filtering, and the second level of filtering be at least some filtering. Another exemplary type of signal processing involves bounding the sensor signal indicative of a parameter of interest (i.e., keeping the signal within a specified range). For example, where there is a determination at step 304 of the activity level of the patient, step 306 can include using a first upper bound and a first lower bound if it is determined that the activity level of the patient does not exceed a threshold, and using a second upper bound and a second lower bound if it is determined at step 306 that the activity level of the patient exceeds the threshold. It is also within the scope of the present invention that no bounding be used if the activity level of the patient does not exceed a threshold, and that specified upper and lower bounds be used if the activity level of the patient exceeds the threshold.

In a specific embodiment useful for where the first implantable sensor is primarily sensitive to body position, step 304 includes using the further implantable sensor(s) to detect body position, and step 306 includes determining, based on the body position detected by the further implantable sensor(s), an extent to which to filter or otherwise process the sensor signal obtained using the first implantable sensor. For example, the further implantable sensor(s) that detects body position can determine whether the patient is supine, or not supine. Thus, at step 304 there can be a determination of whether or not the patient is in a supine position, and at step 306 a first level of filtering and/or other signal processing can be used if it is determined that the patient is supine, and a second level of filtering and/or other signal processing can be used if the patient is not supine, where the second level is greater than the first level. However, it is also within the scope of the present invention that further body positions can be detected, including, but not limited to, sitting, standing and laying facing downward. It is also within the scope of the present invention that for each different type of detectable body position there be a corresponding type of filtering and/or other signal processing to be used.

It is also possible that the first implantable sensor is highly sensitive to both body position and body movement. Where that is the case, step 304 can include using the further implantable sensor(s) to detect both body position and body movement, and step 306 can include determining, based on both the body position and body movement detected by the further implantable sensor(s), an extent to which to filter and/or otherwise process the sensor signal obtained using the first implantable sensor. There can be a different level of filtering/processing used for each of the possible combinations of body position and body movement, or certain combinations may share the same level of filtering/processing. For example, where the further implantable sensor(s) is used to determine that the patient is inactive and supine, then a first level of filtering/processing of the sensor signal obtained using the first implantable sensor can be performed; where the further implantable sensor(s) is used to determine that the patient is inactive but not supine, then a second level of filtering/processing of the sensor signal obtained using the first implantable sensor can be performed; where the further implantable sensor(s) is used to determine that the patient is active and supine, then a third level of filtering/processing of the sensor signal obtained using the first implantable sensor can be performed; and where the further implantable sensor(s) is used to determine that the patient is active and not supine, then a fourth level of filtering/processing of the sensor signal obtained using the first implantable sensor can be performed.

In still another embodiment, where the patient's heart rate is also monitored, step 306 can involve determining, based on the body position and/or body movement and heart rate, an extent to which to filter or otherwise process the sensor signal obtained using the first implantable sensor.

FIG. 4

Embodiments of the present invention also relate to using a sensor(s) that detects body position to determine whether to utilize a signal obtained using another implantable sensor that is sensitive to body position and/or activity. Such embodiments will now be explained with reference to the high level flow diagram of FIG. 4.

Figure 4:
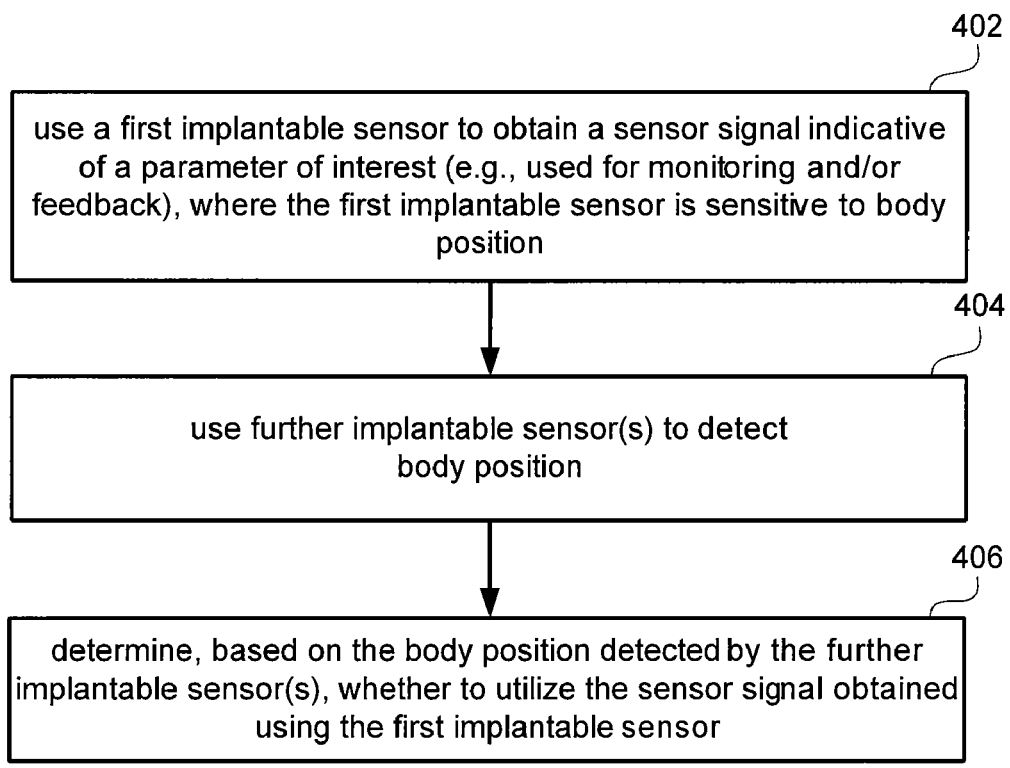
FIG. 4 is a high level flow diagram useful for describing embodiments of the present invention where one or more implantable body position sensor is used to determine whether to utilize a sensor signal of interest obtained using an implantable sensor that is sensitive to body position.

Referring to FIG. 4, at a step 402, a first implantable sensor is used to obtain a sensor signal indicative of a parameter of interest (e.g., that may be used for monitoring and/or feedback), where the first implantable sensor is sensitive to body position. Exemplary types of sensors that are sensitive to body position were discussed above, with reference to step 302 of FIG. 3, and thus need not be discussed again.

At a step 404, one or more further implantable sensor is used to detect the patient's body position. Exemplary types of sensors that can be used to detect body position were discussed above, with reference to step 304 of FIG. 3, and thus need not be discussed again.

At a step 406, there is a determination, based on the body position detected by the further implantable sensor(s), whether to utilize the sensor signal obtained using the first implantable sensor. In certain embodiments, utilizing the sensor signal means using the sensor signal for feedback and/or monitoring purposes, or storing data indicative of the sensor signal for later analysis. In contrast, not using the sensor signal means not using the sensor signal for feedback and/or monitoring purposes, or not storing data indicative of the sensor signal for later analysis. Step 406 can also include putting the first implantable sensor in standby mode when the patient's body position, as detected using the second implantable sensor, is not a desired body position. Examples of possible desired body position include, but are not limited to, supine, sitting up, standing and lying on one's right side or left side.

FIG. 5

Embodiments of the present invention also relate to using a sensor(s) that detects body position and/or body movement to determine how to interpret a signal obtained using another implantable sensor that is sensitive to body position and/or body motion. Such embodiments will be explained below with reference to the high level flow diagram of FIG. 5.

The heart is basically suspended in the thoracic cavity. Depending on whether the patient is lying on their left side, right side, back, front, sitting down or standing up, a signal (e.g., indicative of a cardiac parameter) obtained from a specific sensor may vary. For example, a patient's left atrial pressure (LAP) may be affected by the patient's position, such that a sudden change in position may cause a sudden change in LAP. Thus, it would be useful to know whether a sudden change in LAP was due primarily to a change in body position as opposed to some other factor. Such knowledge can be helpful with determining how to interpret and/or use sensor data. For example, certain sensor data (e.g., respiratory data) may be used one way when a patient is determined to be upright and walking (e.g., used for feedback), but used a different way (e.g., used for monitoring for episodes of apnea) when a patient is determined to be lying down and inactive. For another example, oxygen saturation data may be used to detect asthmatic episodes when a patient is determined to be upright and walking, but used to detect periods of apnea when it is determined that a patient is lying down and inactive (and thus, likely sleeping). This is important because an implantable device's response to an asthmatic episode could be different than the implantable device's response to an apnea episode. Exemplary techniques for an implantable device detecting and treating asthma and apnea are described in U.S. patent application Ser. No. 10/897,372 (Turcott), filed Jul. 21, 2004, entitled "Methods, Systems and Devices for Monitoring Respiratory Disorders", which is incorporated herein by reference. Such embodiments are also useful when a sensor is being used to monitor (e.g., count) how many and/or the longevity of specific types of episodes (e.g., episodes of asthma or apnea).

Figure 5:
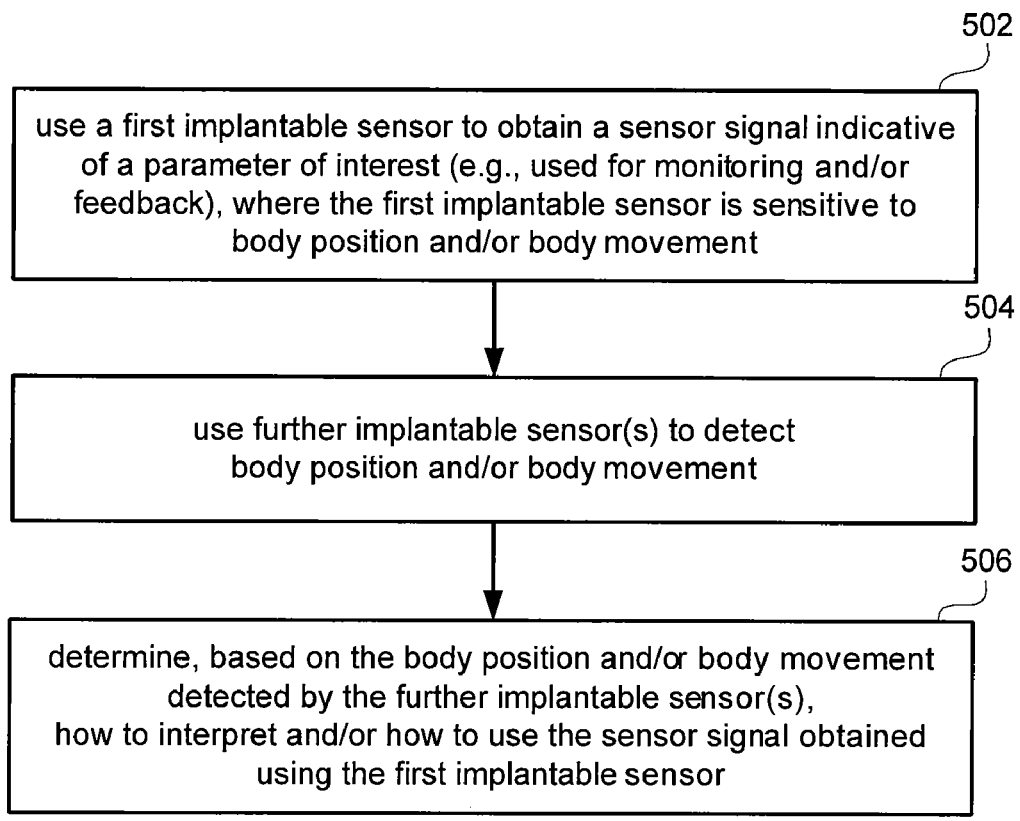
FIG. 5 is a high level flow diagram useful for describing embodiments of the present invention where one or more implantable body position and/or body movement sensor is used to determine how to interpret and/or use a sensor signal of interest obtained using an implantable sensor that is sensitive to body position and/or body movement.

Referring to FIG. 5, at a step 502, a first implantable sensor is used to obtain a sensor signal indicative of a parameter of interest (e.g., that may be used for monitoring and/or feedback), where the first implantable sensor is sensitive to body position and/or body movement. Exemplary types of sensors that are sensitive to body position and/or body movement were discussed above, with reference to step 302 of FIG. 3, and thus need not be discussed again.

At a step 504, one or more further implantable sensor is used to detect the patient's body position and/or body movement. Exemplary types of sensors that can be used to detect body position and/or body movement were discussed above with reference to step 304 of FIG. 3, and thus need not be discussed again.

At a step 506, there is a determination, based on the body position and/or body movement detected by the further implantable sensor(s), of how to interpret and/or how to use the sensor signal obtained using the first implantable sensor. For example, presume the first implantable sensor is a left atrial pressure (LAP) sensor, which produces a sensor signal indicative of a patient's LAP. Also, presume that the LAP sensor is sensitive to both body position and body movement. In such a case, step 406 can include selecting a specific algorithm for monitoring heart failure, based on the patient's body position and/or body movement. Alternatively or additionally, step 506 can include selecting a specific threshold for monitoring heart failure, based on the patient's body position and/or body movement. In other words, data collected from the LAP sensor can be used differently in a same algorithm, used with a different algorithm, and/or compared to a different threshold, based on the body position and/or body movement of the patient as determined using the position and/or movement sensor(s). For another specific example, where the patient is supine and not active, it can be presumed that a signal is minimally or virtually not corrupted. Thus, when a patient is supine and not active, the weight (in an algorithm) given to data collected from an LAP sensor (that is sensitive to body position and/body movement) can be increased; and when the patient is not supine and is active, the weight given to data collected from the LAP sensor can be reduced. For a further example, there can be different constants used in an equation depending on the body position, where such constants could be determined at the time of implant. More specifically, a first constant can be used where the patient is standing, a second constant can be used where the patient is sitting, a third constant can be used where the patient is supine, etc. These are just a few examples of how what is learned from one or more sensors regarding body position and/or body movement can be used to determine how to interpret and/or use a signal (or data thereof) collected from one or more other sensor. One of ordinary skill in the art reading this description will understand that such embodiments can be used in various other manners that are within the scope of the present invention.

FIG. 6

Embodiments of the present invention also relate to using a sensor(s) that detects body position and/or body movement to monitor a condition (e.g., cardiac disease) of a patient. For example, as the heart failure (HF) status of a patient worsens, the patient typically sleeps on his/her right side more often. Tracking the patient's position over time would reveal this. For another example, the body position and/or body movement sensor can be used, together with measures of blood pressure from a further sensor, to detect and treat orthostatic hypotension (e.g., see FIG. 6). Such information can be used alone, or together with information collected from a further sensor (whether or not the further sensor is sensitive to motion), to monitor HF status, another cardiac disease, orthostatic hypotension, or the like. Further, such position and/or movement information can be stored against heart rate, a temporal proximity to a detected tachycardia, etc. Such embodiments will now be explained with reference to the high level flow diagram of FIG. 6A.

Figure 6A:
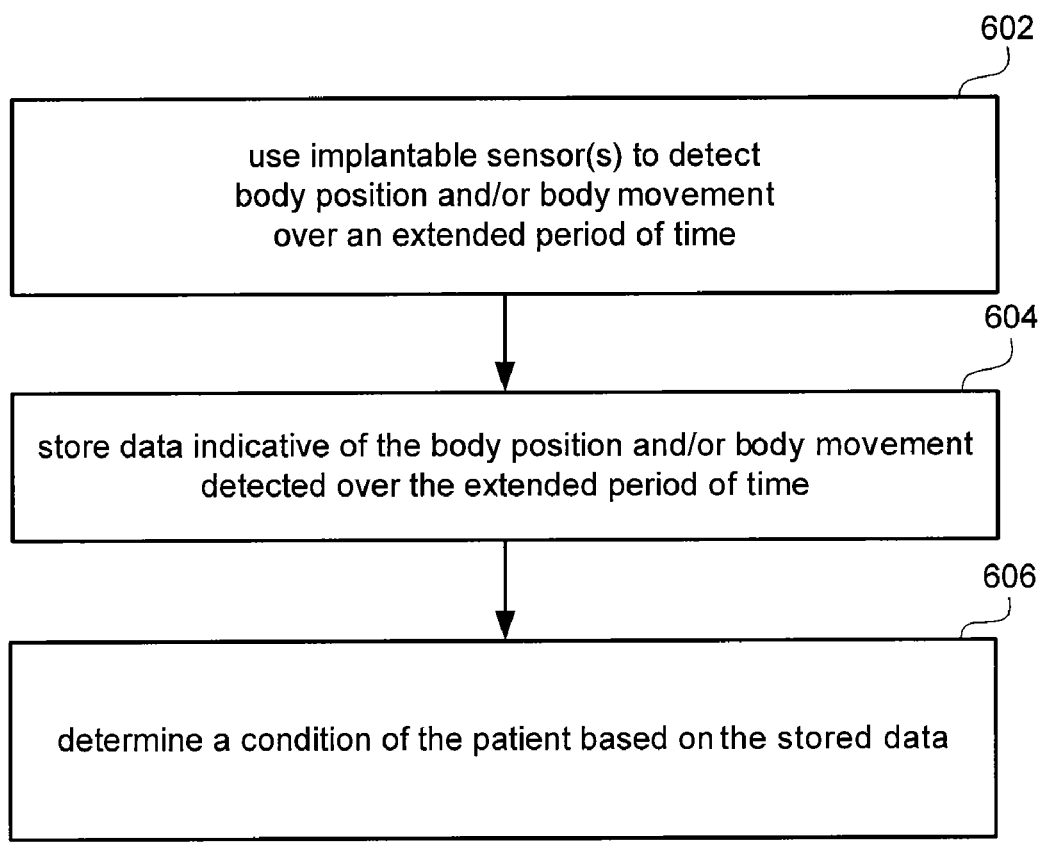
FIG. 6A is a high level flow diagram useful for describing embodiments of the present invention where data relating to body position and/or body movement over an extended period of time is stored and used to determine a condition of the patient.

Referring to FIG. 6A, at a step 602, one or more implantable sensor is used to detect body position and/or body movement over an extended period of time (e.g., 1 hour, 1 day, 1 week, etc.).

At a step 604, data is stored that is indicative of the patient's body position and/or body movement over the extended period of time. For example, data can be time stamped or otherwise stored such that the time it was obtained can be determined.

At a step 606, a condition of the patient is determined based on the stored data. For example, presume that the condition being monitored is HF status, and that an implantable sensor(s) is being used at step 602 to detect a patient's body position for 30 days. Step 604 can include storing data indicative of how often the patient is on his/her right side during each 24 hour period, for 30 consecutive 24 hour periods. In such a case, at step 606 there can be a determination of whether the patient's HF status has worsened, improved or generally stayed the same during those 30 days. For example, if on day 1 the patient spent only 4 hours on his/her right side, but over the 30 days the patient spent more and more time on his/her right side (e.g., by day 30 the patient was spending 6 hours on his/her right side), then it can be determined at step 606 that the patient's HF status has worsened.

Figure 6B:
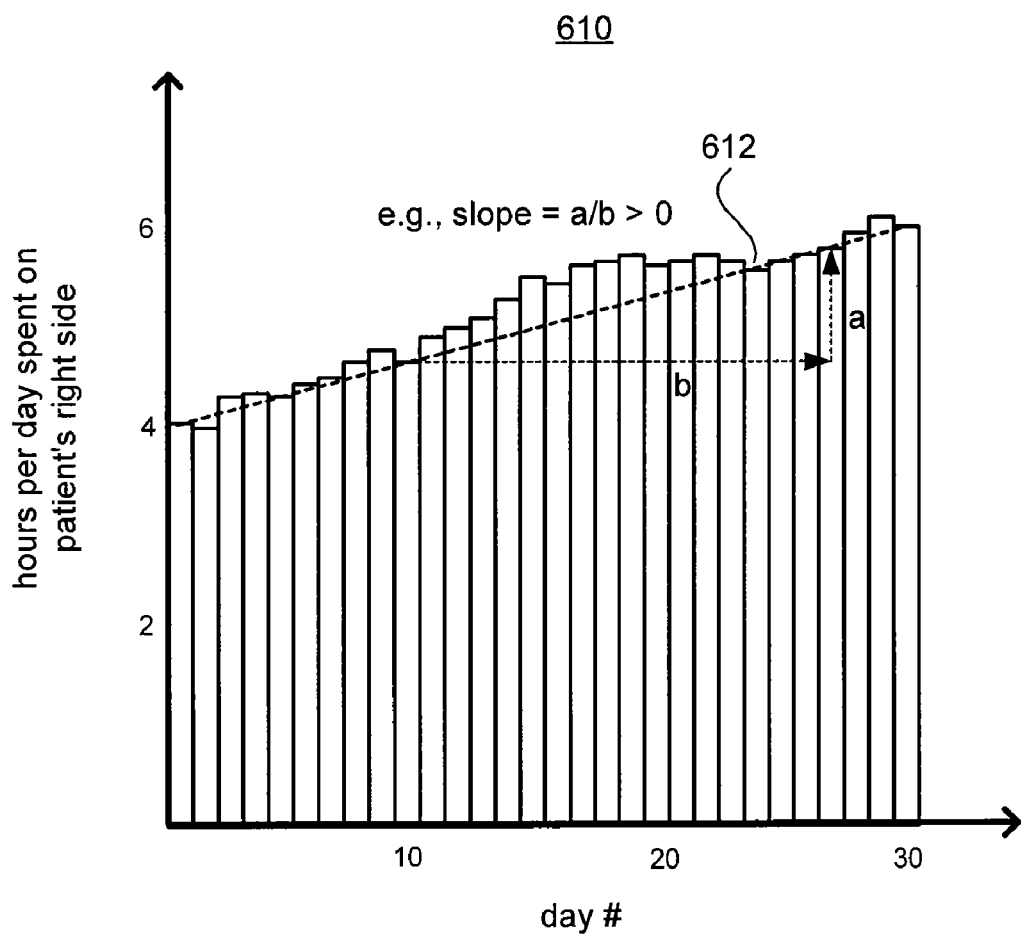
FIG. 6B is a graphical representation of an exemplary histogram that can be generated, stored and analyzed in accordance with the embodiments of FIG. 6A.

Steps 604 and 606 can be accomplished in various manners. For example, step 604 can include producing a histogram indicative of at least one of body position and body movement over the extended period of time; and step 606 can include determining the condition of the patient based on the histogram. Continuing with the above example, each bin or bar of a histogram may be indicative of 1 day, with the magnitude of the bars of the histogram being indicative of the number of hours the patient spent on his/her right side during that day. An example of this is shown in FIG. 6B. An alternative graph, other than a histogram type graph, may also be used.

A histogram or other graph can be analyzed, e.g., by fitting a line to the distribution, determining a slope of that fitted line, and then determining the condition (e.g., change in HF status) based on the slope. An example of this is shown in FIG. 6B, where line 612 is fit to the distribution of the histogram 610. As can be appreciated from FIG. 6, the line 612 has a positive slope, which for the example being discussed, is indicative of a worsening HF status. The slope can be compared to one or more threshold, to determine the extent of the change in status. For a more specific example, the threshold can be zero, so that if the slope is greater than the threshold (i.e., if the slope is positive) then it is determined that HF status has worsened, and if the slope is less than the threshold (i.e., if the slope is negative) then it is determined that HF status has improved. The slope can alternatively be compared to two thresholds, so that change in HF status can be classified worsening, improving or generally staying the same (e.g., if the slope is between the two thresholds). More thresholds can be used to classify the change in HF status or other condition with more granularity. Such threshold values can be predefined or preprogrammed, or can be updated from time to time.

Figure 6C:
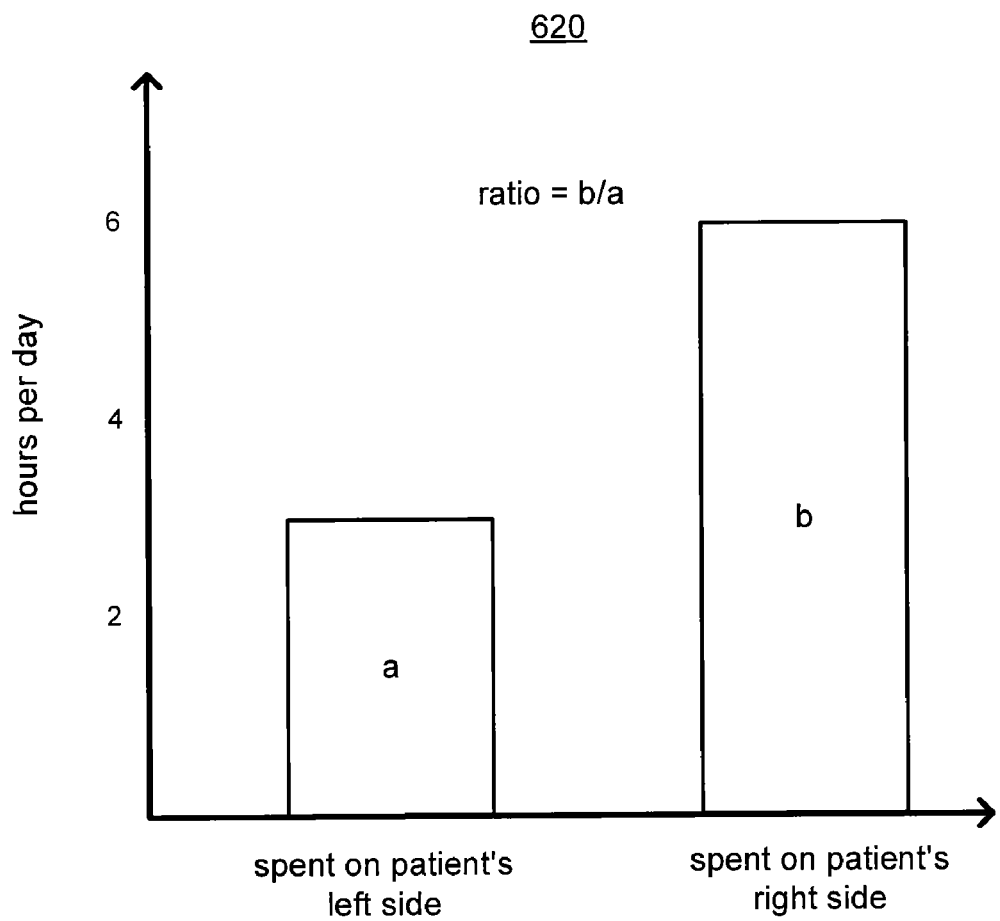
FIG. 6C is a graphical representation of another exemplary histogram that can be generated, stored and analyzed in accordance with the embodiments of FIG. 6A.

An alternative type of histogram is shown in FIG. 6C, which includes a bin or bar indicative of the amount of hours or days the patient spent on his/her left side, and a bin or bar indicative of the amount of hours the patient spend on his/her right side. There can be further bins indicative of further body positions, such as, but not limited to standing, sitting and lying facedown. It is also possible that one bin be indicative of any position that is not lying on one's right side. These are just a few examples. Such a histogram can be produced on a day-to-day basis, and analyzed by fitting a line to the distribution, or by taking a ratio of the two bins. If the ratio is equal to (the amount of hours the patient spent on his/her right side)/(the amount of hours the patient spent on his/her left side), then the magnitude of the ratio would increase as a patient's HF status worsens, and the ratio would decrease as the patient's HF status improves. In accordance with an embodiment, to minimize the amount of data that needs to be stored, at the end of each day the histogram generated for that day can be analyzed, and then only the ratio, slope, or the like, is stored for that day. Such a ratio or slope can later be compared to ratios or slopes determined for later days.

For another example, an activity type sensor can be used to monitor, e.g., on a day-to-day basis, the patient's activity level, thereby enabling a device or practitioner to monitor trends in the patient's overall activity levels. Typically, increases in inactivity are indicative of a problem, such as worsening HF status. Such information can also be used to monitor whether a patient is properly following an exercise regimen that was prescribed to the patient. These are just a few examples of how what is learned from a sensor that detects body position and/or body movement can be used to monitor a condition of a patient over an extended period of time. One of ordinary skill in the art reading this description will understand that such embodiments can be used in various other manners that are within the scope of the present invention.

FIG. 7

Specific embodiment of the present invention, explained with reference to FIG. 7, relates to detecting periods of orthostatic hypotension, which is a sudden fall in blood pressure that occurs when a person assumes a standing position. Orthostatic hypotension may be caused by a decreased amount of blood in the body, resulting from the excessive use of diuretics, vasodilators, or other types of drugs, dehydration, or prolonged bed rest. The disorder may be associated with Addison's disease, a build-up of fatty deposits in the arteries, diabetes, and certain neurological disorders including Shy-Drager syndrome and other dysautonomias. Symptoms, which generally occur after sudden standing, include dizziness, lightheadedness, blurred vision, and temporary loss of consciousness.

Figure 7:
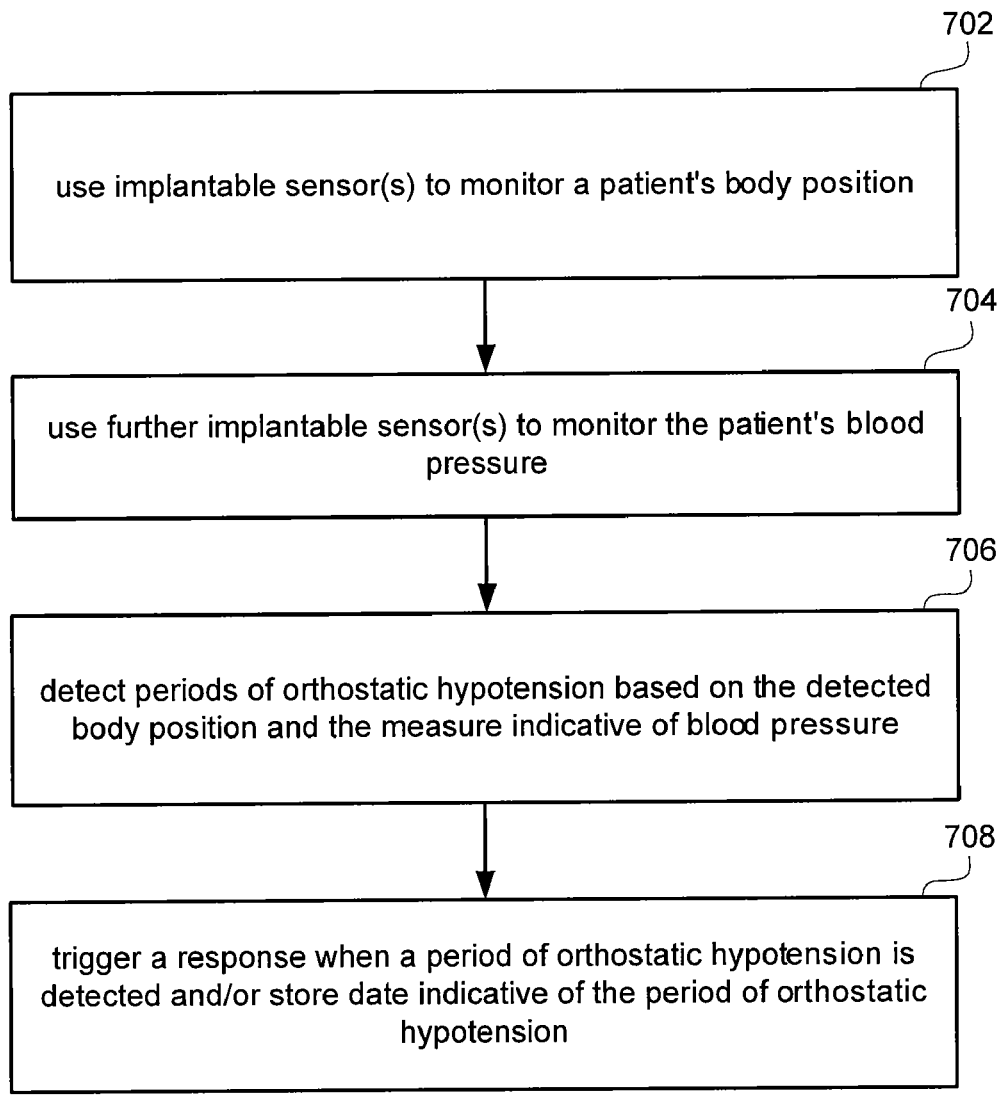
FIG. 7 is a high level flow diagram useful for describing embodiments of the present invention for detecting periods of orthostatic hypotension.

Referring to FIG. 7 at a step 702 an implantable sensor(s) is used to monitor a patient's body position, and at step 704 a further implantable sensor(s) is used to produce a measure indicative of the patient's blood pressure, or otherwise monitor the patient's blood pressure.

At a step 706, periods of orthostatic hypotension are detected based on the detected body position and the measure indicative of blood pressure. For example, step 706 can include detecting a period of orthostatic hypotention when a sudden drop in blood pressure detected at step 704 coincides with a patient changing from a lying or sitting position to a standing position as detected at step 702.

Figure 8:
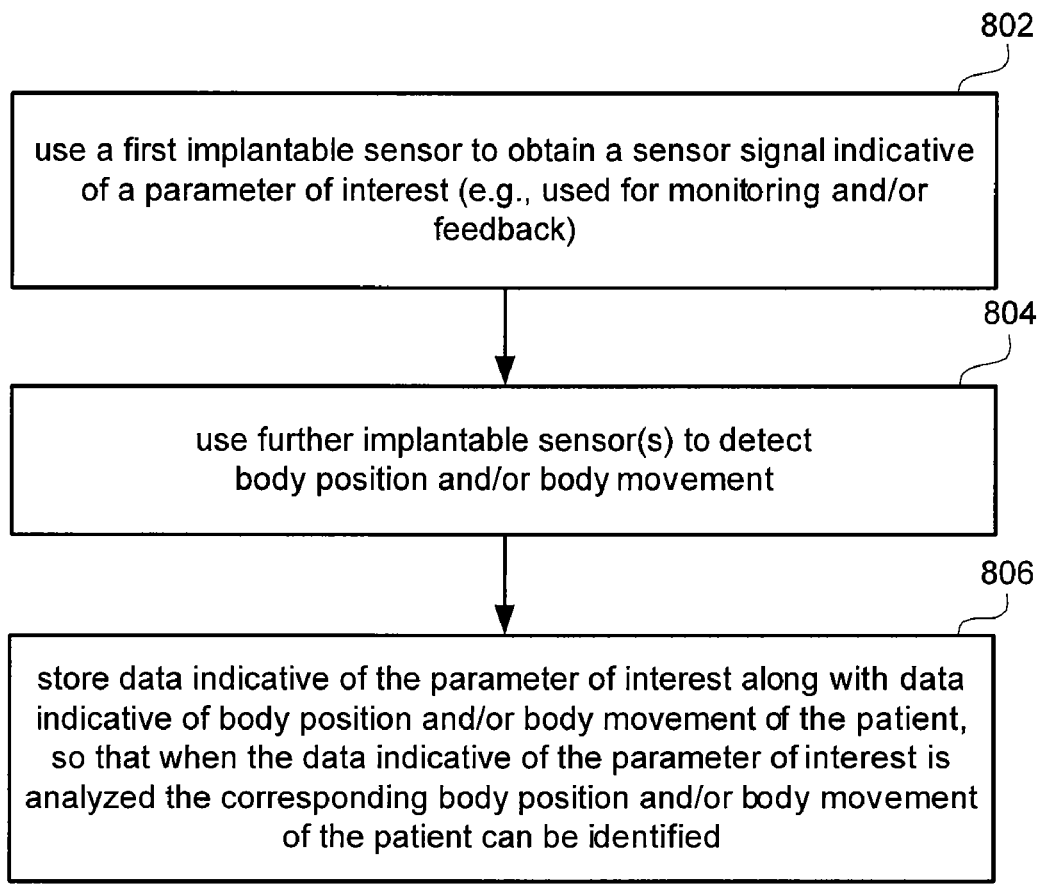
FIG. 8 is a high level flow diagram useful for describing embodiments of the present invention where data indicative of a parameter of interest and data indicative of body position and/or body motion data are collected and stored so that when the data indicative of the parameter of interest is analyzed the corresponding body position and/or body movement can be identified.

At a step 708, a treatment is triggered in response to detecting a period of orthostatic hypotension. An example of such a treatment can be, but is not limited to, increasing a patient's pacing rate. Another possible treatment can be stimulation of a vagal nerve to increase vagal tone. Alternatively, or additionally, at step 708 data indicative of detected periods of orthostatic hypotension are stored. Such data can be indicative of the time and extent of the period, as well as the patient's body position(s) and blood pressure.
FIG. 8

Embodiments of the present invention also relate to collecting and storing data indicative of a parameter of interest along with data indicative of body position and/or body motion, so that when the data indicative of the parameter of interest is analyzed the corresponding body position and/or body movement can be identified. Such embodiments will be described with reference to FIG. 8.

Referring to FIG. 8, at a step 802, a first implantable sensor is used to obtain a sensor signal indicative of a parameter of interest (e.g., used for monitoring and/or feedback). Such an implantable sensor may or may not be sensitive to body position and/or body motion. Exemplary types of sensor that can be used to obtain a sensor signal indicative of a parameter of interest include, but are not limited to, a PPG sensor, a pulse oximetry sensor, a pressure sensor (e.g., sensor for measuring left atrial pressure) and a glucose sensor. The sensor signal can be indicative of, e.g., a hemodynamic, physiologic, respiratory or rhythmic cardiac function, such as, but not limited to respiration, left atrial pressure, right atrial pressure, thoracic impedance, arterial O2 saturation, ventricular O2 saturation, photoplethysmography, mechanical contractility, heart sounds, blood glucose concentration, mechanical synchrony, cardiogenic impedance, etc.

At a step 804, one or more further implantable sensor is used to detect the patient's body position and/or body movement. Exemplary types of sensors that can be used to detect body position and body motion were discussed above, and thus need not be discussed again.

As indicated at step 806, data indicative of the parameter of interest is stored (e.g., in a memory within the implantable device) along with data indicative of at least one of body position and body movement of the patient, so that when the data indicative of the parameter of interest is analyzed the corresponding body position and/or body movement of the patient can be identified. For example, this would enable determinations of what position a patient was in when the patient experienced a tachycardia, or an elevated LAP, etc. More generally, this would enable a device or a practitioner to correlate body position and/or body movement, as detected using a sensor for detecting the same, with events or conditions detected using other sensors.

In specific embodiments, time-correlated histograms of position and a parameter of interest (e.g., LAP) are saved. It is also within the scope of the present invention to only save position information when a parameter of interest (e.g., LAP) goes outside a specified range. For example, if a patient's LAP is being monitored by an implantable device, the device may only save information indicative of the patient's position (together with LAP information) whenever the patient's LAP goes outside a specified range. Another option is to have a table with LAP ranges, specifying that when LAP was between values A and B, that patient was on his/her left side 80% of the time, his/her right side 10% of the time, and supine 10% of the time; and when LAP was between values C and D, the patient was on his/her left side 10% of the time, and his/her right side 90% of the time, etc. A physician can then tailor therapy based on this information. For example, if the physician observes that LAP is not good every time the patient is on his/her right side, the physician can program the implantable device to increase the pacing rate or release some drug whenever patient goes into that position, to prevent LAP from changing.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed:

1. In an implantable system, a method for improving the use of an implantable sensor that is sensitive to body position and body movement, the method comprising:
   (a) using a first implantable sensor to obtain a sensor signal indicative of a parameter of interest used to monitor a first medical disorder of a patient and to obtain feedback for adjusting parameters of an implantable device to treat a second medical disorder of the patient, where the first implantable sensor is sensitive to body position and a body movement;
   (b) using a second implantable sensor to detect and determine the identity of a first multidimensional body position and detect a first body movement when the patient is in the first body position and has the first body movement;
   (c) using the second implantable sensor to detect and determine the identity of a second multidimensional body position and second body movement when the patient is in the second body position and has the second body movement;
   (d) using the sensor signal obtained using the first implantable sensor to obtain feedback for adjusting parameters of an implantable device to treat the second disorder of the patient when the first body position and first body movement are detected and identified; and
   (e) using the sensor signal obtained using the first implantable sensor to monitor and not treat the first disorder of the patient when the second body position and second body movement are detected and identified.

2. The method of claim 1 further comprising:
   using the second implantable sensor and/or a third implantable sensor to detect at least one of a third body position and third body movement when the patient is in the third body position and/or has the third body movement; and
   using the sensor signal obtained using the first implantable sensor to obtain feedback for adjusting parameters of an implantable device to treat the second disorder of the patient when the third body position is identified and/or third body movement is detected, wherein:

using the sensor signal obtained using the first implantable sensor to monitor the first disorder when the patient is in the second body position and has the second body movement comprises selecting a first algorithm based on the second body position and second body movement, using the sensor signal obtained using the first implantable sensor to monitor the first disorder when the patient is in the third body position and/or has the third body movement comprises selecting a second algorithm based on the at least one of a third body position and third body movement, and the first algorithm is different from the second algorithm.

3. The method of claim 1 further comprising:

using the second implantable sensor to detect at least one of a third body position and third body movement when the patient is in the third body position and/or has the third body movement; and in the sensor signal obtained using the first implantable sensor to obtain feedback for adjusting parameters of an implantable device to treat the second disorder of the patient when the third body position is identified and/or third body movement is detected, wherein:

using the sensor signal obtained using the first implantable sensor to monitor the first disorder when the patient is in the second body position and has the second body movement comprises selecting a first threshold for monitoring the first disorder based on the second body position and second body movement, and using the sensor signal obtained using the first implantable sensor to monitor the first disorder when the patient is in the third body position and/or has the third both movement comprises selecting a second threshold for monitoring the first disorder based on the third body position and third body movement, and the first threshold is different from the second threshold.

4. The method of claim 1 further comprising:

using the second implantable sensor to detect at least one of a third body position and third body movement when the patient is in the third body position and/or has the third body movement; and using the sensor signal obtained using the first implantable sensor to obtain feedback for adjusting parameters of an implantable device to treat the second disorder of the patient when the third body position is identified and/or third body movement is detected, wherein:

using the sensor signal obtained using the first implantable sensor to monitor the first disorder when the patient is, in the second body position and has the second body movement comprises selecting a first constant for use in an equation for monitoring the patient's first disorder based on the at least one of a second body position and second body movement using the sensor signal obtained using the first implantable sensor to monitor the first disorder when the patient is in the third body position and/or has the third body movement comprises selecting a second constant for use in an equation for monitoring a patient disorder based on the at least one of a third body position and third body movement, and the first constant is different from the second constant.

5. The method of claim wherein the identity of the multi-dimensional body position is one of a supine, not supine, sitting, standing, lying, lying on a right side, lying on a left side, and upright position.

6. An implantable system, comprising:

a first implantable sensor configured to obtain a sensor signal indicative of a parameter of interest that is used for at least one of monitoring at least a first disorder of a patient and feedback for adjusting parameters of an implantable device to treat at least a second, different disorder of the patient, where the first implantable sensor is sensitive to body position and body movement;

a second implantable sensor configured to detect at least one of body position and body movement; and a processing unit configured to determine, based on the body position and body movement detected by the second implantable sensor, whether to use the sensor signal obtained using the first implantable sensor to monitor and not treat at least the first disorder of the patient or as feedback for adjusting parameters of the implantable device to treat at least the second disorder of the patient.

7. The implantable system of claim 6 further comprising a third implantable sensor configured to detect a body position and body movement wherein the processing unit is further configured to determine, based on the at least one of body position and body movement detected by at least the second implantable sensor, whether to monitor at least a third patient disorder, wherein the third patient disorder is different from the first and second patient disorder.

8. The implantable system of claim 6 wherein the sensor signal obtained by the first implantable sensor comprises oxygen saturation data and the processing unit is further configured to use the oxygen saturation data for monitoring asthmatic episodes when the second implant sensor detects a patient is upright and walking and the processing unit is further configured to use the oxygen saturation data to monitor periods of apnea when the second implant sensor detects the patient is lying down and inactive.

9. The implantable system of claim 6 wherein the processing unit is further configured to determine based on both the body position and body movement detected by the second implantable sensor, whether to use the sensor signal obtained using the first implantable sensor for monitoring at least the first disorder of the patient or for feedback for adjusting parameters of the implantable device to treat at least the second disorder of the patient.

10. The implantable system of claim 9 wherein the sensor signal comprises respiratory data and the processing unit uses the respiratory data for feedback when the second implant sensor detects a patient is upright and walking and the processing unit uses the respiratory data for monitoring for episodes of apnea when the second implant sensor detects the patient is lying down and inactive.

11. The implantable system of claim 6 wherein the processing unit is further configured to use the sensor signal obtained using the first implantable sensor to monitor the first disorder of the patient when the second body position is identified and second body movement is detected, wherein using the sensor signal obtained using the first implantable sensor to monitor the first disorder comprises selecting based on the at least one of body position and body movement detected by the second implantable sensor, a specific algorithm to use to monitor at least the patient's first disorder.

12. The implantable system of claim 11 wherein the first implantable sensor is a left atrial pressure (LAP) sensor and the patient's first disorder is heart failure.

13. The implantable system of claim 6 wherein the processing unit is further configured to use the sensor signal obtained using the first implantable sensor to monitor the first condition of the patient when the second body position is identified and second body movement is detected, wherein using the sensor signal obtained using the first implantable sensor to monitor the first condition comprises selecting, based on the at least one of body position and body movement detected by at least the second implantable sensor, which threshold to use to monitor at least the patient's first disorder.

14. The implantable system of claim 6 wherein the first implantable sensor is a photoplethysmography (PPG) sensor.

15. The implantable system of claim 6 wherein the first implantable sensor is an impedance sensor.

16. The implantable system of claim 6 wherein the first implantable sensor is an oxygen saturation sensor.

17. The implantable system of claim 6 wherein the first implantable sensor is a glucose sensor.

18. In an implantable system, a method for monitoring a condition of a patient, the method comprising:
   (a) using at least one implantable sensor to detect time-correlated data of how often a patient sleeps on his or her right side, by detecting at least one of body position and body movement over an extended period of time;
   (b) storing the time-correlated data indicative of how often patient sleeps on his or her right time detected over the extended period of time, by producing a histogram indicative of the at least one of body position and body movement and
   (c) determining a status of cardiac disease of the patient based on the stored data.

19. The implantable system of claim 18, wherein the method further comprises using a second implantable sensor to detect a parameter of interest over an extended period of time.

20. The system of claim 19, wherein the data indicative of at least one of body position or body movement is stored only when the parameter of interest goes outside of a specific range.

21. The system of claim 20, wherein the parameter of interest is left atrial pressure (LAP).

* * * * *